(12) United States Patent
Ruffin

(10) Patent No.: US 11,607,546 B2
(45) Date of Patent: Mar. 21, 2023

(54) COCHLEAR IMPLANT

(71) Applicant: The Trustees of Indiana University, Indianapolis, IN (US)

(72) Inventor: Chad Victor Ruffin, Indianapolis, IN (US)

(73) Assignee: The Trustees of Indiana University, Bloomington, IN (US)

(*) Notice: Subject to any disclaimer, the term of this patent is extended or adjusted under 35 U.S.C. 154(b) by 207 days.

(21) Appl. No.: 16/482,539

(22) PCT Filed: Feb. 1, 2018

(86) PCT No.: PCT/US2018/016454
§ 371 (c)(1),
(2) Date: Jul. 31, 2019

(87) PCT Pub. No.: WO2018/144732
PCT Pub. Date: Aug. 9, 2018

(65) Prior Publication Data
US 2021/0128918 A1 May 6, 2021

Related U.S. Application Data

(60) Provisional application No. 62/453,105, filed on Feb. 1, 2017.

(51) Int. Cl.
*A61N 1/36* (2006.01)
*A61N 1/05* (2006.01)

(52) U.S. Cl.
CPC ....... *A61N 1/36038* (2017.08); *A61N 1/0541* (2013.01)

(58) Field of Classification Search
CPC .......... A61N 1/05; A61N 1/0541; A61N 1/36; A61N 1/36038
See application file for complete search history.

(56) References Cited

U.S. PATENT DOCUMENTS

| | | | | |
|---|---|---|---|---|
| 4,532,930 A | * | 8/1985 | Crosby | A61N 1/36039 607/57 |
| 4,593,696 A | * | 6/1986 | Hochmair | A61N 1/36038 607/57 |

(Continued)

OTHER PUBLICATIONS

International Search Report and Written Opinion issued by the ISA/US, Commissioner for Patents, dated Apr. 12, 2018, for International Application No. PCT/US2018/016454.

(Continued)

*Primary Examiner* — Christopher A Flory
(74) *Attorney, Agent, or Firm* — Hartman Global IP Law; Gary M. Hartman; Domenica N. S. Hartman

(57) ABSTRACT

A dichotic pulsatile and analog stimulation system, comprises a first cochlear implant device implanted in one ear of a patient; and a second cochlear implant device implanted in another ear of the patient; wherein the first cochlear implant device comprises a first speech processor configured to provide single channel analog stimulation to a first electrode array mounted to a cochlea of the one ear and the second cochlear implant device comprises a second speech processor configured to provide interleaved pulse stimulation to a second electrode array mounted to a cochlea of the other ear.

21 Claims, 2 Drawing Sheets

(56) References Cited

U.S. PATENT DOCUMENTS

| | | | |
|---|---|---|---|
| 5,549,658 A * | 8/1996 | Shannon | A61N 1/36038 607/57 |
| 5,626,629 A * | 5/1997 | Faltys | A61N 1/36038 607/57 |
| 6,289,247 B1 | 9/2001 | Faltys et al. | |
| 6,575,894 B2 * | 6/2003 | Leysieffer | A61N 1/36036 600/25 |
| 7,043,303 B1 * | 5/2006 | Overstreet | A61N 1/36039 607/57 |
| 7,117,038 B1 * | 10/2006 | Overstreet | A61N 1/36038 607/57 |
| 7,376,563 B2 * | 5/2008 | Leysieffer | A61N 1/36039 704/271 |
| 7,496,406 B1 * | 2/2009 | Segel | A61N 1/36038 607/136 |
| 7,571,005 B1 * | 8/2009 | Segel | A61N 1/36038 607/57 |
| 7,835,799 B1 * | 11/2010 | Segel | A61N 1/36038 607/57 |
| 7,835,800 B1 * | 11/2010 | Segel | A61N 1/36038 607/57 |
| 7,860,572 B2 * | 12/2010 | Ibrahim | A61N 1/36038 607/57 |
| 8,027,733 B1 * | 9/2011 | Fridman | A61N 1/36039 607/57 |
| 8,165,689 B1 * | 4/2012 | Saoji | A61N 1/0541 607/57 |
| 8,699,734 B1 * | 4/2014 | Haller | A61N 1/36038 381/318 |
| 2002/0099421 A1 * | 7/2002 | Goldsmith | A61N 1/37229 607/55 |
| 2004/0030376 A1 | 2/2004 | Gibson et al. | |
| 2005/0137651 A1 * | 6/2005 | Litvak | A61N 1/37247 607/57 |
| 2005/0197679 A1 | 9/2005 | Dawson | |
| 2005/0209657 A1 * | 9/2005 | Chung | A61N 1/36038 607/57 |
| 2006/0100672 A1 | 5/2006 | Litvak | |
| 2009/0264961 A1 * | 10/2009 | Schleich | A61N 1/36039 607/57 |
| 2009/0264962 A1 * | 10/2009 | Faltys | A61N 1/36038 607/57 |
| 2009/0264963 A1 * | 10/2009 | Faltys | A61N 1/36038 607/57 |
| 2009/0312820 A1 | 12/2009 | Nie et al. | |
| 2010/0198300 A1 * | 8/2010 | Smith | A61N 1/36038 607/57 |
| 2012/0239392 A1 * | 9/2012 | Mauger | G10L 21/0216 704/226 |
| 2013/0218237 A1 * | 8/2013 | Svirsky | A61N 1/36039 607/57 |
| 2014/0074184 A1 * | 3/2014 | Litvak | H04R 25/50 607/57 |
| 2014/0214123 A1 * | 7/2014 | Janssen | H04R 25/552 607/57 |
| 2014/0222104 A1 * | 8/2014 | Smith | A61N 1/36038 607/57 |
| 2015/0039052 A1 * | 2/2015 | van Dijk | A61N 1/37252 607/57 |
| 2015/0201287 A1 * | 7/2015 | Jespersgaard | H04R 25/407 381/321 |
| 2016/0136425 A1 * | 5/2016 | Hamacher | H04R 25/407 607/57 |
| 2016/0165363 A1 * | 6/2016 | Meister | H04R 25/552 607/57 |
| 2016/0206879 A1 * | 7/2016 | Smith | A61N 1/36038 |
| 2016/0277849 A1 * | 9/2016 | Strauss | A61N 1/36038 |
| 2017/0064462 A1 * | 3/2017 | Warren | H04R 25/353 |
| 2017/0080228 A1 * | 3/2017 | Meister | A61N 1/36038 |
| 2017/0224980 A1 * | 8/2017 | Grasso | A61N 1/36036 |
| 2018/0071541 A1 * | 3/2018 | Meskens | A61N 1/36038 |
| 2019/0046116 A1 * | 2/2019 | Shah | A61N 1/0541 |
| 2019/0151661 A1 * | 5/2019 | Li | A61N 1/37211 |
| 2020/0168238 A1 * | 5/2020 | Mauger | G10L 21/0216 |
| 2020/0213781 A1 * | 7/2020 | Case | A61N 1/36036 |
| 2020/0215338 A1 * | 7/2020 | Meskens | A61N 1/36038 |

OTHER PUBLICATIONS

International Preliminary Report on Patentability received for PCT Patent Application No. PCT/US2018/016454, dated Aug. 15, 2019, 5 pages.

* cited by examiner

COCHLEAR IMPLANT

CROSS-REFERENCE TO RELATED APPLICATIONS

The present application is a U.S. national stage under 35 U.S.C. § 371 of International Application No. PCT/US2018/016454, filed on Feb. 1, 2018, which claims the benefit of and priority to U.S. Provisional Application No. 62/453,105, filed on Feb. 1, 2017, and entitled "COCHLEAR IMPLANT," the entire contents of which being expressly incorporated herein by reference in their entireties.

TECHNICAL FIELD

The present invention relates generally to cochlear implants and more specifically to a system and method for simultaneously employing analog and digital processing strategies across the ears of a cochlear implant user.

BACKGROUND

Cochlear implants are limited in their ability to provide sufficient pitch cues for perception of speech in noise, music and auditory cognition that approaches normal hearing listeners. Cochlear implants often consist of implantable electrode arrays consisting of multiple electrodes under the control of an external sound processor that is designed to bypass damaged inner ear structures and create a perception of sound by directly stimulating afferents of the auditory nerve. There are two conventional paradigms by which electrode arrays may be stimulated. One is by modulating an analog, electrical wave on the electrode array in response to incoming sound ("analog stimulation"). The other is by modulating a series of electrical pulses ("pulsatile stimulation") in response to incoming sound. Analog stimulation was created in the 1960s and 1970s and later abandoned as the overlap of electrical fields on adjacent electrodes distorted the perceived sound. Thus, an interleaved pulsatile stimulation strategy whereby a series of pulses are delivered sequentially or in paired fashion. This discharge pattern was designed to mitigate the channel interaction that results from simultaneous activation of multiple adjacent channels. Variants of these interleaved strategies have been developed in which adjacent electrodes are discharged in a coordination fashion to create virtual channels between the two channels. However, these interleaved strategies are lacking in temporal resolution. This results in a decrease in pitch perception of interleaved speech processing strategies relative to even a single channel/electrode of analog stimulation.

Pitch is important for, among other things, segregating voices in noisy environments based on the fundamental frequency of the voice. Ideally, pitch is delivered via two different mechanisms (1) spectral pitch and (2) temporal pitch. Spectral pitch is conveyed by the location of stimulation on the electrode array (e.g., an electrode stimulated further into the cochlea is perceived as lower in pitch). Temporal pitch is conveyed by the rate of discharge on a single electrode. Interleaved pulsatile strategies primarily work by conveying spectral pitch and very little by temporal pitch. Conversely, a single channel of analog stimulation by virtue of temporal pitch can convey more pitch information than 16 electrodes/channels of an interleaved strategy. Unfortunately, multiple channels of analog stimulation during which electrodes are simultaneously discharging electrical current creates overlapping electrical fields. Thus, outcomes for multichannel delivery of pulsatile information are relatively better as users are able to derive more information from multiple electrodes which are isolated in time.

As further described below, the analog strategy was clinically abandoned in the early 2000s, after which attention was turned to providing additional channels (electrodes) of information with bilateral cochlear implantation. Even with bilateral cochlear implants and other speech processing strategies, there are electrophysiological constraints to creating auditory nerve discharge patterns that mimic those of the non-deafened ear. Accordingly, a need exists for an improved stimulation strategy for cochlear implant users.

SUMMARY

According to one embodiment, the present disclosure provides a dichotic pulsatile and analog stimulation system, comprising: a first cochlear implant device implanted in one ear of a patient; and a second cochlear implant device implanted in another ear of the patient; wherein the first cochlear implant device comprises a first speech processor configured to provide at least one of actual single channel analog stimulation or effective single channel stimulation to a first electrode array mounted to a cochlea of the one ear and the second cochlear implant device comprises a second speech processor configured to provide interleaved pulse stimulation to a second electrode array mounted to a cochlea of the other ear. In one aspect of this embodiment, the second cochlear implant device is a multichannel digital implant device. In another aspect, the interleaved pulse stimulation includes a series of interleaved signals of constant pulse width. In yet another aspect, the first cochlear implant device includes a first microphone and a first transmitter, the first speech processor, the first microphone and the first transmitter being configured to mount to a first external surface of the patient. In a variant of this aspect, the first cochlear implant further includes a first surgically implanted receiver coupled to the first electrode array. In a further variant, the first surgically implanted receiver is configured to wirelessly receive excitation signals from the first transmitter and convert the excitation signals for transmission to the first electrode array. In still a further variant, the first electrode array is configured to apply signals received from the first receiver to a plurality of regions of an auditory nerve associated with the cochlea of the one ear. In another variant of this aspect, the second cochlear implant device incudes a second microphone and a second transmitter, the second speech processor, the second microphone and the second transmitter being configured to mount to a second external surface of the patient. In a further variant, the second cochlear implant device further includes a second surgically implanted receiver coupled to the second electrode array. In yet a further variant, the second electrode array is configured to apply signals received from the second receiver to a plurality of regions of an auditory nerve associated with the cochlea of the other ear. In another aspect of this embodiment, the first cochlear implant device is a multi-electrode device programmed to function as a single channel device.

According to another embodiment, the present disclosure provides a method of improving hearing of a patient having a hearing impairment, comprising: mounting a first cochlear implant device for operation with one ear of the patient; mounting a second cochlear implant device for operation with another ear of the patient; configuring a first speech processor of the first cochlear implant device to provide at least one of actual single channel analog stimulation or effective single channel analog stimulation to a first electrode array of the first cochlear implant device mounted to a cochlea of the one ear; and configuring a second speed processor of the second cochlear implant device to provide interleaved pulse stimulation to a second electrode array of the second cochlear implant device mounted to a cochlea of the other ear. In one aspect of this embodiment, the second cochlear implant device is a multichannel pulsatile implant device. In another aspect, the interleaved pulse stimulation includes a series of interleaved signals of constant pulse width. In another aspect, the first cochlear implant device includes a first microphone and a first transmitter, and mounting the first cochlear implant device includes mounting the first speech processor, the first microphone and the first transmitter to a first external surface of the patient. In a variant of this aspect, mounting the first cochlear implant device includes surgically implanting a first receiver coupled to the first electrode array. A further variant further comprises wirelessly receiving excitation signals from the first transmitter and converting the excitation signals for transmission to the first electrode. In still a further variant, the first electrode array is configured to apply signals received from the first receiver to a plurality of regions of an auditory nerve associated with the cochlea of the one ear. In another variant, the second cochlear implant device incudes a second microphone and a second transmitter, and mounting the second cochlear implant device includes mounting the second speech processor, the second microphone and the second transmitter to a second external surface of the patient. In another variant, mounting the second cochlear implant device further includes surgically implanting a second receiver coupled to the second electrode array. In yet another variant, the second electrode array is configured to apply signals received from the second receiver to a plurality of regions of an auditory nerve associated with the cochlea of the other ear. In another aspect, the first cochlear implant device is a multi-electrode device programmed to function as a single channel device. Yet another aspect further comprises mapping the first and the second cochlear implant devices to the patient by testing the patient's ability to understand sound information in a plurality of environments.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The above-mentioned and other features of this disclosure and the manner of obtaining them will become more apparent and the disclosure itself will be better understood by reference to the following description of embodiments of the present disclosure taken in conjunction with the accompanying drawings, wherein.

Figure 1:
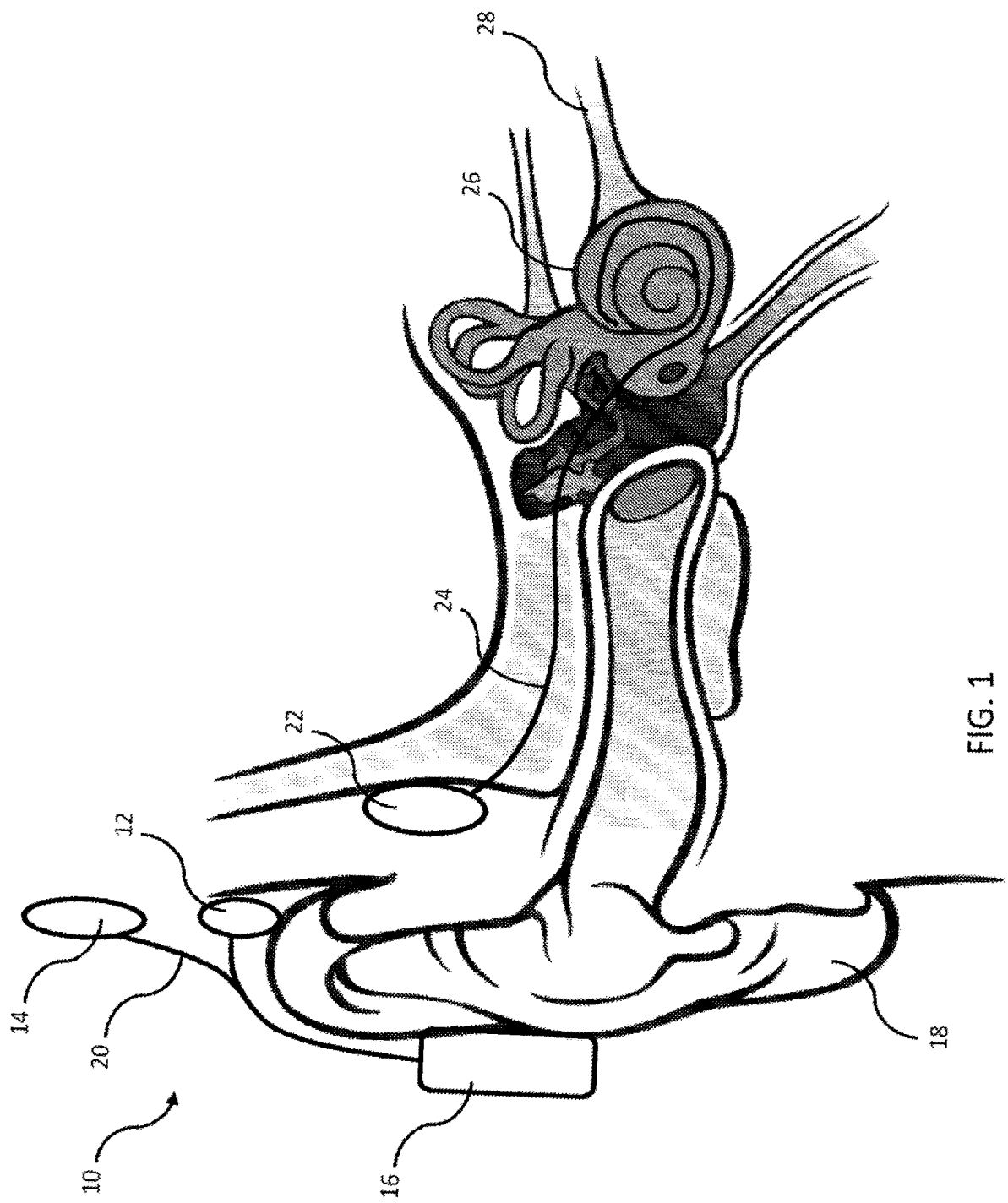
FIG. 1 is a conceptual drawing of a cochlear implant.

While the present disclosure is amenable to various modifications and alternative forms, specific embodiments have been shown by way of example in the drawings and are described in detail below. The present disclosure, however, is not to limit the particular embodiments described. On the contrary, the present disclosure is intended to cover all modifications, equivalents, and alternatives falling within the scope of the appended claims.

DETAILED DESCRIPTION

One of ordinary skill in the art will realize that the embodiments provided can be implemented in hardware, software, firmware, and/or a combination thereof. Programming code according to the embodiments can be implemented in any viable programming language such as Assembly, C, C++, Python, HTML, XTML, JAVA or any other viable high-level programming language, or a combination of a high-level programming language and a lower level programming language.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

A Dichotic Pulsatile and Analog Stimulation System (DPASS) according to the present disclosure is a speech processing strategy for cochlear implants that is a departure from the current method of providing an identical paradigm of speech processing strategies on each ear of a bilateral cochlear implant user. Classically the gold-standard speech processing strategy is a series of interleaved pulses on each implanted ear. DPASS aims to provide a single channel of analog stimulation in one ear and a pulsatile strategy in the opposite ear to increase the sound information available to the patient.

Research has shown that harnessing any residual hearing of a deaf patient significantly improves hearing performance. Some of these methods include providing (1) a hearing aid on the opposite, non-implanted ear, (2) using hybrid cochlear implants in which a hearing aid and partial cochlear implant electrode array are provided in the same ear and (3) providing a cochlear implant to patients with a deaf ear and normal hearing in the contralateral one ear. Collectively, these three methods have conclusively shown that acoustic and electrical speech information can be integrated by the central nervous system to improve hearing.

The present disclosure aims to harness these findings. For those with two cochlear implants, one ear will receive a single channel of analog stimulation while the opposite ear receives a clinically available pulsatile strategy. DPASS is a novel way of stimulating cochlear implants and will therefore likely require a similar one-year adjustment period on the part of patient while the brain learns to integrate the new information.

Referring now to FIG. 1, a cochlear implant 10 is shown mounted on/implanted in a user. Implant 10 is a surgically implanted electrical device generally used by people who are profoundly deaf or hard of hearing. Implant 10 differs from a hearing aid in that it does not simply amplify sound. Instead, implant 10 bypasses the damaged parts of the inner ear to provide sound signals to the auditory nerve and thus, to the patient's brain. Implant 10 generally includes a microphone 12, a transmitter 14 and a speech processor 16, all of which are mounted externally to the patient's ear 18. Microphone 12 and transmitter 14 are connected to speech processor 16 by wiring harness 20. Implant 10 further includes a surgically implanted receiver 22 and an electrode array 24 coupled to receiver 22. Electrode array 24 extends into the inner ear and applies signals to the cochlea 26 which are received by the auditory nerve 28.

In use, microphone 12 picks up sound from the environment and transmits corresponding signals to speech processor 16 via wiring harness 20. Speech processor 16 processes the signals in a manner further described herein and transmits excitation signals to transmitter 14. Transmitter 14 transmits the excitation signals wirelessly to receiver 22, which converts the signals into a form suitable for transmission on array 24. Array 24 receives the signals from receiver 22 and applies the signals to different regions of auditory nerve 28. Implants such as implant 10 are manufactured by a plurality of companies including Advanced Bionics, Cochlear Corp., Neuotron, Oticon, and Med El.

The designs of cochlear implants and the corresponding standard of care have evolved over time. In the late 1970s, single channel analog cochlear implants became available. In the early 1980s, multichannel interleaved/digital and multichannel analog implants were introduced. Around 2001, the analog speech processing strategies were essentially abandoned, and the pulsatile implants became the de facto standard of care. In 2004, bilateral digital cochlear implants were introduced and became the standard of care. It was discovered in 2013 that a single electrode of analog stimulation delivers more pitch information than even a large number of pulsatile electrodes. Also, between around 2010 through around 2016, it was determined that the brains of patients with single sided deafness can integrate sound from both normal and implanted ears.

Figure 2:
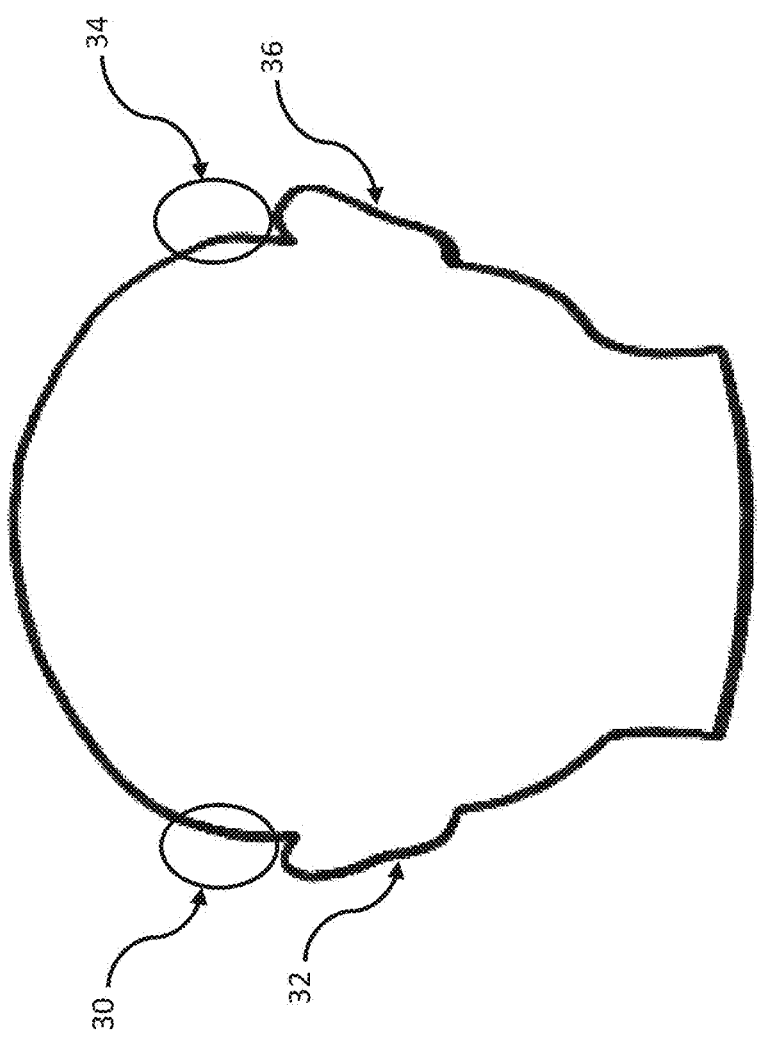
FIG. 2 is a schematic diagram of a bilateral cochlear implant system according to the teaching of the present disclosure.

According to the present disclosure and referring to FIG. 2, a patient is outfitted with an analog speech processing implant 30 in one ear 32 and a newer style pulsatile speech processing implant 34 in the other ear 36 to improve the hearing experience. The implants 30, 34 are "mapped" to the patient by testing the patient's ability to understand conversation in quiet and noisy environments, to appreciate music, to identify other cues in speech (e.g., the gender, identity and emotion of a speaker), and to determine the location from which a voice or sound originates. Cognitive factors may be tested or assessed and incorporated into the map. Essentially, the user provides feedback to a computer regarding threshold detection levels and comfortable levels of electrical current associated with stimulation in various frequency ranges applied to the electrode array. The perceived loudness may be adjusted for each electrode (much like an equalizer is used to adjust the output of an audio system) and frequency ranges assigned to an electrode.

Further mappings, typically about once per year (and when the implant is originally implanted), are made to the speech processing strategy based on the mapping tests.

In this manner, the patient should have improved perception of words in speech in quiet and noisy environments, as well as improved recognition of dialect, speaker identification, gender, health, noises and music. The teachings according to the present disclosure may also result in better integration of the speech signal, less mental energy spent processing the degraded incoming speech signal, and improved memory for all things. In other words, cognition may improve with improved quality of sound, even if absolute hearing does not improve.

It should be understood that the hardware associated with implant 30 is essentially the same as the hardware associated with implant 34. The speech processor 16 of the implants differs in that implant 30 provides analog stimulation and implant 34 provides digital stimulation. Implant 30 may be a single channel device that provides direct actual single channel analog stimulation to an electrode array or a device that provides effective single channel analog stimulation by combining the output of adjacent electrodes to steer the field and provide what is effectively single channel operation. In the latter case, adjacent electrodes are discharged to steer the current and create virtual channels between adjacent hardware channels. In other words, implant 30 may be a multi-electrode device programmed to behave as a single channel device. Implant 34 is preferably a multi-channel device but may in alternative embodiments, have a single channel.

It is known in the art that full access to the speech signal depends on access to "envelope" cues and "fine structure cues". For hearing in quiet environments, a few channels of envelope cues are generally sufficient. This provides "spectral pitch" so that the user can hear vowels and consonants in non-demanding conditions. However, for noisy environments, more channels of envelope are needed to achieve better performance (hence multichannel implants), but even then, performance plateaus. This is because a listener needs more fine pitch information to segregate the pitch of a speaker's voice from others in multiple-talker noise. A single channel of an analog stimulation has the ability to transmit "fine structure" (fine pitch) cues. However, for most users, a single channel of analog stimulation will not be sufficient to perceive speech. To hear consonant sounds, more than one channel of information is needed (the vocal part of a speech signal can be delivered by a single electrode)—i.e., several channels of envelope or fine structure.

As indicated above, multiple channels of analog stimulation do not work well as a result of channel to channel interaction. The system and method according to the present disclosure provides the fine pitch cues on ear 32 with analog stimulation from implant 30 and some pitch, but mostly envelope across several channels on ear 34 with pulsatile stimulation from implant 34. This approach is a direct departure from conventional approaches and the trajectory of development of cochlear implants. As indicated above, single channel cochlear implants using analog strategies in which filtered sound modulates a current were developed in the 1970s and scaled up to multiple electrode strategies in the 1980s. During this time, multichannel cochlear implants were developed using interleaved pulses of constant pulse width on each electrode. The analog strategies were effective in encoding instantaneous frequency (i.e., zero crossings) and the pulsatile strategies with fixed pulse widths were effective in encoding the energy within a frequency band. On the other hand, the analog strategies, in which each electrode is simultaneously discharging electrical current, suffered as a result of channel interaction, and the pulsatile strategies, which activate only one array electrode at a time, resulted in degraded temporal resolution.

Nonetheless, given that implants using constant pulse width pulses were so much more successful than either single or multichannel analog implants, all analog strategies were abandoned in the early 2000s. Subsequently, there were attempts to improve the temporal resolution issues associated with pulsatile strategies including using faster rates, increasing the number of channels with current steering to produce virtual channels between the actual channels, and incorporating pulse widths that varied based on the fundamental frequency of the input signal. None of this development led in a direction of decreasing the number of electrodes on the array either via programming or using manufacturing techniques. Moreover, during all of this research, each ear was treated as an independent entity, and no strategy for one ear required the other ear to function. An example of requiring two cochlear implants would be true binaural strategies where timing differences in the arrival of sound are exploited to improve binaural/stereo hearing, an approach which has never been exploited clinically. Further, no cochlear implant manufacturer has attempted to incorporate wholly different strategies on either ear to allow the brain to differentially extract information. The principles of the present disclosure include aspects that exploit benefits of such unconventional approaches.

The connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus Various modifications and additions can be made to the exemplary embodiments discussed without departing from the scope of the present disclosure. For example, while the embodments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:

1. A method of improving hearing of a patient having a hearing impairment by implanting a dichotic pulsatile and analog stimulation system in ears of the patient, the dichotic pulsatile and analog stimulation system comprising:
   a first cochlear implant device configured to be implanted in a first ear of the ears of the patient; and
   a second cochlear implant device configured to be implanted in a second ear of the ears of the patient;
   wherein the first cochlear implant device comprises a first speech processor configured to provide a single channel of analog stimulation comprising at least one of actual single channel analog stimulation and effective single channel analog stimulation to a first electrode array configured to be placed within a cochlea of the first ear and the second cochlear implant device comprises a second speech processor configured to provide interleaved pulse stimulation to a second electrode array configured to be mounted to a cochlea of the second ear;
   wherein the first and second cochlear implant devices are both multi-electrode devices but the first speech processor of the first cochlear implant device is programmed to function as a single channel device and differs from the second speech processor by delivering the single channel of analog stimulation to the first electrode array;
   wherein the method comprises:
   mounting the first cochlear implant device for operation with the first ear of the patient by locating the first electrode array within the cochlea of the first ear;
   mounting the second cochlear implant device for operation with the second ear of the patient;
   operating the first speech processor of the first cochlear implant device to deliver the single channel of analog stimulation to a single location within the cochlea of the first ear with a single electrode of the first electrode array that is located at the single location or with adjacent electrodes of the first electrode array that are located adjacent to the single location; and
   operating the second speech processor to provide the interleaved pulse stimulation to the second electrode array.

2. The method of claim 1, wherein the second cochlear implant device is a multichannel digital implant device.

3. The method of claim 1, wherein the interleaved pulse stimulation includes a series of interleaved signals of constant pulse width.

4. The method of claim 1, wherein the first cochlear implant device includes a first microphone and a first transmitter, the first speech processor, the first microphone and the first transmitter being configured to mount to a first external surface of the patient.

5. The method of claim 4, wherein the first cochlear implant further includes a first receiver configured to be surgically implanted and coupled to the first electrode array.

6. The method of claim 5, wherein the first receiver is configured to wirelessly receive excitation signals from the first transmitter and convert the excitation signals for transmission to the first electrode array.

7. The method of claim 6, wherein the first electrode array is configured to apply signals received from the first receiver to a plurality of regions of an auditory nerve associated with the cochlea of the first ear.

8. The method of claim 4, wherein the second cochlear implant device includes a second microphone and a second transmitter, the second speech processor, the second microphone and the second transmitter being configured to mount to a second external surface of the patient.

9. The method of claim 8, wherein the second cochlear implant device further includes a second receiver configured to be surgically implanted and coupled to the second electrode array.

10. The method of claim 9, wherein the second electrode array is configured to apply signals received from the second receiver to a plurality of regions of an auditory nerve associated with the cochlea of the second ear.

11. A method of improving hearing of a patient having a hearing impairment, the method comprising:
providing first and second cochlear implant devices that are both multi-electrode devices, the first cochlear implant device comprising a first speech processor and a first electrode array, the second cochlear implant device comprising a second speech processor and a second electrode array, the first speech processor being programmed to function as a single channel device and deliver to the first electrode array a single channel of analog stimulation comprising at least one of actual single channel analog stimulation and effective single channel analog stimulation;
mounting the first cochlear implant device for operation with a first ear of the patient by locating the first electrode array within the cochlea of the first ear;
mounting the second cochlear implant device for operation with a second ear of the patient;
operating the first speech processor of the first cochlear implant device to deliver the single channel of analog stimulation to a single location within the cochlea of the first ear with a single electrode of the first electrode array that is located at the single location or with adjacent electrodes of the first electrode array that are located adjacent to the single location;
operating the second speech processor of the second cochlear implant device to provide interleaved pulse stimulation to the second electrode array within the cochlea of the second ear; and
mapping the first and second cochlear implant devices to the patient on the basis of the ability of the patient to understand conversations in environments that differ in noise levels, understand speech cues, and determine locations from which sounds originate;
wherein the mapping comprises the patient providing feedback regarding threshold detection levels and comfortable levels of electrical current associated with stimulation in frequency ranges applied to electrodes of the first and second electrode arrays, and then adjusting perceived loudness for the first and second electrode arrays and frequency ranges assigned to the single electrode or the adjacent electrodes of the first electrode array and to the electrodes of the second electrode array.

12. The method of claim 11, wherein the second cochlear implant device is a multichannel pulsatile implant device.

13. The method of claim 11, wherein the interleaved pulse stimulation includes a series of interleaved signals of constant pulse width.

14. The method of claim 11, wherein the first cochlear implant device includes a first microphone and a first transmitter, and mounting the first cochlear implant device includes mounting the first speech processor, the first microphone and the first transmitter to a first external surface of the patient.

15. The method of claim 14, wherein mounting the first cochlear implant device includes surgically implanting a first receiver coupled to the first electrode array.

16. The method of claim 15, further comprising wirelessly receiving excitation signals from the first transmitter and converting the excitation signals for transmission to the first electrode.

17. The method of claim 16, wherein the first electrode array is configured to apply signals received from the first receiver to a plurality of regions of an auditory nerve associated with the cochlea of the first ear.

18. The method of claim 14, wherein the second cochlear implant device includes a second microphone and a second transmitter, and mounting the second cochlear implant device includes mounting the second speech processor, the second microphone and the second transmitter to a second external surface of the patient.

19. The method of claim 18, wherein mounting the second cochlear implant device further includes surgically implanting a second receiver coupled to the second electrode array.

20. The method of claim 19, wherein the second electrode array is configured to apply signals received from the second receiver to a plurality of regions of an auditory nerve associated with the cochlea of the second ear.

21. The method of claim 11, wherein the first cochlear implant device is a multi-electrode device programmed to function as a single channel device.

* * * * *